United States Patent [19]

Bagli et al.

[11] 4,375,470

[45] Mar. 1, 1983

[54] 2(1-PIPERAZINYL)-CYCLOHEP-TIMIDAZOLE ANTIHYPERTENSIVE COMPOSITION AND METHODS

[75] Inventors: Jehan F. Bagli, Kirkland; Tibor Bogri, Montreal, both of Canada

[73] Assignee: American Home Products Corporation, New York, N.Y.

[21] Appl. No.: 198,024

[22] Filed: Oct. 17, 1980

Related U.S. Application Data

[62] Division of Ser. No. 118,343, Feb. 4, 1980, Pat. No. 4,258,188.

[51] Int. Cl.$^3$ ............... A61K 31/495; C07D 401/14; C07D 403/04

[52] U.S. Cl. ..................... 424/250; 544/139; 544/364; 544/370; 544/382

[58] Field of Search .......................... 424/250

[56] References Cited

U.S. PATENT DOCUMENTS

| | | | |
|---|---|---|---|
| 3,461,131 | 8/1969 | Sunagawa et al. | 548/302 |
| 3,849,431 | 11/1974 | Gallay et al. | 544/370 |
| 4,093,726 | 6/1978 | Winn et al. | 544/370 |

*Primary Examiner*—Donald G. Daus
*Assistant Examiner*—James H. Turnipseed
*Attorney, Agent, or Firm*—Arthur E. Wilfond

[57] ABSTRACT

2-(1-Piperazinyl)-cycloheptimidazole derivatives are disclosed. The foregoing compounds are useful antihypertensive agents.

3 Claims, No Drawings

2(1-PIPERAZINYL)-CYCLOHEPTIMIDAZOLE ANTIHYPERTENSIVE COMPOSITION AND METHODS

This is a division, of application Ser. No. 118,343, filed Feb. 4, 1980 and now U.S. Pat. No. 4,258,188.

BACKGROUND OF THE INVENTION

This invention relates to novel 2-(1-piperazinyl)-cycloheptimidazole derivatives, to a process for their preparation and to therapeutically acceptable acid addition salts and pharmaceutical compositions of the derivatives. These derivatives are useful for treating hypertension in mammals.

Illustrative of references obtainable from a literature search for cycloheptimidazole derivatives is U.S. Pat. No. 3,461,131 to G. Sunagawa et al., Aug. 12, 1969. Of the cycloheptimidazole derivatives, the 2-(substituted amino)-cycloheptimidazole derivatives exemplified by U.S. Pat. No. 3,461,131, cited above, can be considered most closely related to the compounds of this invention. However, the compounds of this invention have a piperazinyl ring instead of the amino group at position 2 of the cycloheptimidazole ring system of said patent.

SUMMARY OF THE INVENTION

The compounds of this invention are represented by formula I

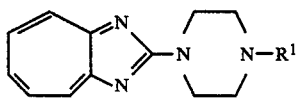
(I)

in which $R^1$ is hydrogen, lower alkyl, lower alkenyl, lower alkynyl, hydroxy(lower)alkyl, lower alkoxycarbonyl, formyl, phenyl(lower)alkyl, phenylcarbonyl, 2- or 3-furanylcarbonyl, phenyl, 2- or 3-pyridinyl, 1-oxo(-lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl-α-phenylmethyl or phenyl substituted with one or two members selected from the group consisting of halo, lower alkyl, lower alkoxy or trifluoromethyl.

A preferred class of compounds of formula I is one in which $R^1$ is hydrogen lower alkyl, lower alkenyl, lower alkynyl, hydroxy(lower)alkyl, lower alkoxycarbonyl, formyl, phenyl(lower)alkyl, phenylcarbonyl, 2-furanylcarbonyl, phenyl, 2-pyridinyl, 1-oxo(lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl-α-phenylmethyl or phenyl substituted with one member selected from the group consisting of halo, lower alkyl, lower alkoxy or trifluoromethyl.

Still another preferred class of compounds of formula I is one in which $R^1$ is hydrogen, lower alkyl, lower alkenyl, lower alkynyl, hydroxy(lower)alkyl, lower alkoxycarbonyl, formyl, 2-furanylcarbonyl, 1-oxo(-lower)alkoxy(lower)alkyl, aminoiminomethyl, hydrazinothioxomethyl or sodium thiothioxomethyl.

The therapeutically acceptable acid addition salts of the compounds of formula I also are included within the scope of this invention.

The compounds of formula I can form a pharmaceutical composition comprising a compound of formula I, or a therapeutically acceptable acid addition salt thereof, and a pharmaceutically acceptable carrier.

The compunds of this invention can be used to treat hypertension in a hypertensive mammal by administering to the mammal an effective antihypertensive amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 2-methylpropyl, pentyl, hexyl and the like, unless stated otherwise.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "lower alkynyl" as used herein means straight chain alkynyl radicals containing from two to six carbon atoms and branched chain alkynyl radicals containing four carbon atoms and includes ethynyl, 2-propynyl, 1-methyl-2-propynyl, 3-hexynyl and the like.

The term "lower alkenyl" as used herein means straight chain alkenyl radicals containing from two to six carbon atoms and branched chain alkenyl radicals containing three or four carbon atoms and includes ethenyl, 2-methyl-2-propenyl, 4-hexenyl and the like.

The term "lower alkanol" as used herein means both straight and branched chain alkanols containing from one to four carbon atoms and includes methanol, ethanol, isopropanol, butanol and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethyl-morpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or therapeutically acceptable acid addition salts thereof is demonstrated in standard pharmacological tests, for example, in tests conducted in the spontaneously hypertensive rat (SHR) using the testing method described by I. Varva, et al., Can. J. Physiol. Pharmacol., 51, 727 (1973). The latter test method is modified so that the test compound is administered orally to the rat by gastric gavage and the blood pressure is measured by the tail-cuff method before administration of the compound and up to 4 hours thereafter. The examples referred to hereinbelow are corresponding examples in the aforementioned parent application Ser. No. 118,343 from which the instant application is a division. Using this method, the following representative compounds of formula I are effective for reducing the blood pressure (BP) in the spontaneously hypertensive rat (the amount of test compound and its reduction in BP are indicated in the parentheses): 4-(2-cycloheptimidazolyl)piperazine-1-carboxylic acid ethyl ester (described in Example 1, at a dose of 1.0 mg/kg of body weight causes a 20% decrease in mean BP at 30 minutes), 2-(1-piperazinyl)cycloheptimidazole hydrochloride (described in Example 2, at a dose of 25 mg/kg of body weight causes a 14% decrease in mean BP at 4 hours), 4-(2-cycloheptimidazolyl)-1-piperazinecarboximidamide hydroiodide trihydrate (described in Example 3, at a dose of 10 mg/kg of body weight causes a 19% decrease in mean BP at 1 hour), 4-(2-cycloheptimidazolyl)-piperazine-1-carboxylic acid 2-methylpropyl ester (described in Example 4, at a dose of 25 mg/kg of body weight causes a 15% decrease in mean BP at 1 hour), 2-[4-(2-propenyl)-1-piperazinyl]-cycloheptimidazole (described in Example 5, at a dose of 10 mg/kg of body weight causes a 18% decrease in mean BP at 1 hour), 2-[4-(2-propynyl)-1-piperazinyl]-cycloheptimidazole (described in Example 5, at a dose of 25 mg/kg of body weight causes a 13% decrease in mean BP at 1 hour), 4-(2-cycloheptimidazolyl)-piperazine-1-carbothioic acid, sodium salt (described in Example 6, at a dose of 25 mg/kg of body weight causes a 16% decrease in mean BP at 4 hours), 4-(2-cycloheptimidazolyl)-piperazine-1-carbothioic acid hydrazide (described in Example 8, at a dose of 5 mg/kg of body weight causes a 21% decrease in mean BP at 1 hour), 2-(4-methyl-1-piperazinyl)cycloheptimidazole hydrochloride (described in Example 13, at a dose of 25 mg/kg of body weight causes a 10% decrease in mean BP at 4 hours), 2-[4-(2-furanylcarbonyl)-1-piperazinyl]-cycloheptimidazole (described in Example 14, at a dose of 50 mg/kg of body weight causes a 19% decrease in systolic BP at 1.5 hours), 2-(4-formyl-1-piperazinyl)cycloheptimidazole (described in Example 14, at a dose of 10 mg/kg of body weight causes a 19% decrease in mean BP at 1 hour), 4-(2-cycloheptimidazolyl)-1-piperazineethanol (described in Example 15, at a dose of 10 mg/kg of body weight causes a 19% decrease in mean BP at 1 hour) and 2,2-dimethylpropanoic acid, 2-[4-(2-cycloheptimidazolyl)-1-piperazinyl]ethyl ester (described in Example 16, at a dose of 10 mg/kg of body weight causes a 16 to 25% decrease in mean BP at 1 hour).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a delayed and/or sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects.

For example, the effective antihypertensive amount of the compounds for oral administration usually ranges from about 0.1 mg to about 250 mg per kilogram body weight per day in single or divided doses although as aforementioned variations will occur. However a dosage level that is in the range of from about 1.0 to about 100 mg per kilogram body weight per day in single or divided doses is employed most desirably for oral administration in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triameterene and furosemide. Examples of still other suitable antihypertensive agents are prazosin, hydralazine and centrally active antihypertensive agents such as methyldopa, clonidine, and reserpine; as well as the β-adrenergic blocking agents, for instance, propranolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing duiretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physician Desk Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt is administered as described previously.

We claim:

1. An antihypertensive pharmaceutical composition, which comprises an effective amount of a compound of

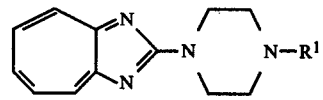

in which $R^1$- is hydrogen, lower alkyl, lower alkenyl, lower alkynyl, hydroxy(lower)alkyl, lower alkoxycarbonyl, formyl, phenyl(lower)alkyl, phenylcarbonyl, 2- or 3-furanylcarbonyl, phenyl, 2- or 3-pyridinyl, 1-oxo(-lower)alkoxy(lower)alkyl, 2-imidazolinyl, aminoiminomethyl, aminothioxomethyl, (lower alkylamino)thioxomethyl, (phenylamino)thioxomethyl, hydrazinothioxomethyl, (lower alkylthio)thioxomethyl, sodium thiothioxomethyl, α-halophenyl- α-phenylmethyl or phenyl substituted with one or two members selected from the group consisting of halo, lower alkyl, lower alkoxy or trifluoromethyl; or a therapeutically acceptable acid addition salt thereof and a pharmaceutically acceptable carrier therefor.

2. A method of treating hypertension in a mammal, which comprises administering to said mammal an effective antihypertensive amount of a compound of claim 1.

3. A method of treating hypertension in a hypertensive mammal, which comprises administering to the mammal an antihypertensive effective amount of a compound of claim 1 in combination with an effective amount of an agent selected from the group consisting of a diuretic agent, an antihypertensive agent and a diuretic agent in combination with an antihypertensive agent.

* * * * *